US00PP32238P3

(12) United States Plant Patent
Lubell-Brand et al.

(10) Patent No.: US PP32,238 P3
(45) Date of Patent: Sep. 29, 2020

(54) SWEETFERN PLANT NAMED 'BLUE SEA'

(50) Latin Name: *Comptonia peregrina*
Varietal Denomination: Blue Sea

(71) Applicant: University of Connecticut, Farmington, CT (US)

(72) Inventors: Jessica Lubell-Brand, Willington, CT (US); Mark Henry Brand, Willington, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 16/501,905

(22) Filed: Jul. 1, 2019

(65) Prior Publication Data

US 2020/0053938 P1 Feb. 13, 2020

Related U.S. Application Data

(60) Provisional application No. 62/764,585, filed on Aug. 10, 2018.

(51) Int. Cl.
*A01H 5/00* (2018.01)
*A01H 6/00* (2018.01)
*A01H 9/00* (2006.01)

(52) U.S. Cl.
USPC ..... Plt./226
CPC ..... *A01H 9/00* (2013.01)

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — Michael Best & Friedrich LLP

(57) ABSTRACT

The present invention relates to new and distinct cultivar of the woody-stemmed shrub, Sweetfern, botanically known as *Comptonia peregrina* and referred to by the name 'Blue Sea'. 'Blue Sea' is a compact, blue-tinted leaf Sweetfern plant that has leaves that are narrower and finer in texture than wild *Comptonia peregrina.*

2 Drawing Sheets

Latin name of the genus and species: *Comptonia peregrina.*

Variety denomination: 'Blue Sea'.

BACKGROUND OF THE INVENTION

The present invention relates to a new and distinct cultivar of Sweetfern plant, botanically known as *Comptonia peregrina* and hereinafter referred to by the name 'Blue Sea'. The plant is a woody-stemmed shrub whose common name is "Sweetfern." This name is given because the plant's foliage resembles leaflets of some ferns and the plant emits an aroma similar to the smell of some ferns. Sweetfern is difficult to produce from seed and stem cuttings. Currently, rhizomes are harvested from the wild but produce an inferior highly variable crop, which does not meet the need of the growing demand. Also, rhizome division is labor intensive and yields relatively few plants. Current practices involving rhizomes result in an inferior product and irregular supply. The disclosed new and distinct Sweetfern cultivar 'Blue Sea' allows growers to reliably produce a uniform, high quality shrub product.

The new Sweetfern plant is a product of a planned breeding program conducted by the Inventors in Storrs, Conn. The objective of the breeding program is to develop new uniform, dense, fine-textured *Comptonia* plants with blue-green foliage and good propagation and container performance. The new Sweetfern plant originated from an open-pollination in spring 2010 in Storrs, Conn., of an unnamed proprietary plant of *Comptonia peregrina*, not patented, as the female, or seed, parent with an unknown selection of *Comptonia peregrina* as the male, or pollen, parent. Seedlings were evaluated from 2011 to 2016, and the new Sweetfern plant was discovered and selected by the Inventors during the spring of 2016 as a single plant from within the progeny of the stated open-pollination in Storrs, Conn.

Asexual reproduction of the new Sweetfern plant by softwood shoot cuttings in a controlled greenhouse environment in Storrs, Conn., since 2012 has shown that the unique features of this new Sweetfern plant are stable and reproduced true to type in successive generations of asexual reproduction.

The Inventors optimized propagation by cuttings to achieve ~80% success. The cuttings were taken early in the growth cycle when shoots were first emerging following dormancy. Cuttings sourced from container plants in hoop houses were obtained in late March to early May and taken from recently expanded (in a young physiological state) shoots when the shoots had emerged and elongated to a length of 2 to 3 inches. The shoots were cut close to the stem from which it emerged. Wounding of the slender stems was not needed. The cuttings were dipped in indolebutyric acid (IBA) in talc at 3000 (Hormodin 2) or 8000 ppm (Hormodin 3) and stuck in 50 plug trays or another propagation container filled with media composed of 1:1:1 of peat:perlite: vermiculite and set in mist. The cuttings were provided with 30 to 50% shade when rooting. The cuttings rooted in 4 to 6 weeks and were then up-potted.

SUMMARY OF THE INVENTION

Plants of the new Sweetfern have not been observed under all possible environmental conditions and cultural practices.

The phenotype may vary somewhat with variations in environmental conditions such as temperature and light intensity without, however, any variance in genotype.

The following traits have been repeatedly observed and are determined to be the unique characteristics of 'Blue Sea': Grows 2 to 3 feet tall (~60 cm to ~90 cm) with a similar spread. Plants are densely branched with a mounded habit. Because the plant is rhizomatous and spreads by underground stems, the number of branches varies. A plant of 18 inches (46 cm) tall by 24 inches (60 cm) in diameter typically has 10 to 12 branches. The alternate simple leaves are linear (5 to 10 cm long and 1 to 1.5 cm wide) with coarsely toothed margins. 'Blue Sea' exhibits uniformly dark green foliage with a blue cast to the foliage. The fine textured leaves are uniformly dark green with a blue tint. Plants are monoecious, but the inflorescences are small and not ornamentally significant. These characteristics in combination distinguish 'Blue Sea' as a new and distinct Sweetfern plant:

1. Compact habit;
2. Dense branching;
3. Uniform, fine textured foliage;
4. Narrow, dark green, and blue-tinted leaves; and
5. Landscape adaptability equivalent to wild plants.

Plants of the new Sweetfern can be compared to wild-type Sweetfern plants. Plants of the new Sweetfern differ from wild-type Sweetfern plants in the following characteristics:

1. Plants of the new Sweetfern are more compact, dense, and uniform than wild-type Sweetfern.
2. Leaves of the new Sweetfern are darker green in color than leaves of wild-type Sweetfern and have a blue tint.
3. Leaves of the new Sweetfern are narrower and finer in texture than leaves of wild-type Sweetfern.

BRIEF DESCRIPTION OF THE PHOTOGRAPHS

The accompanying colored photographs illustrate the overall appearance of the new Sweetfern plant showing the colors as true as it is reasonably possible to obtain in colored reproductions of this type. Colors in the photographs may differ slightly from the color values cited in the detailed botanical description, which accurately describe the colors of the new Sweetfern plant.

DETAILED BOTANICAL DESCRIPTION

Figure 1:
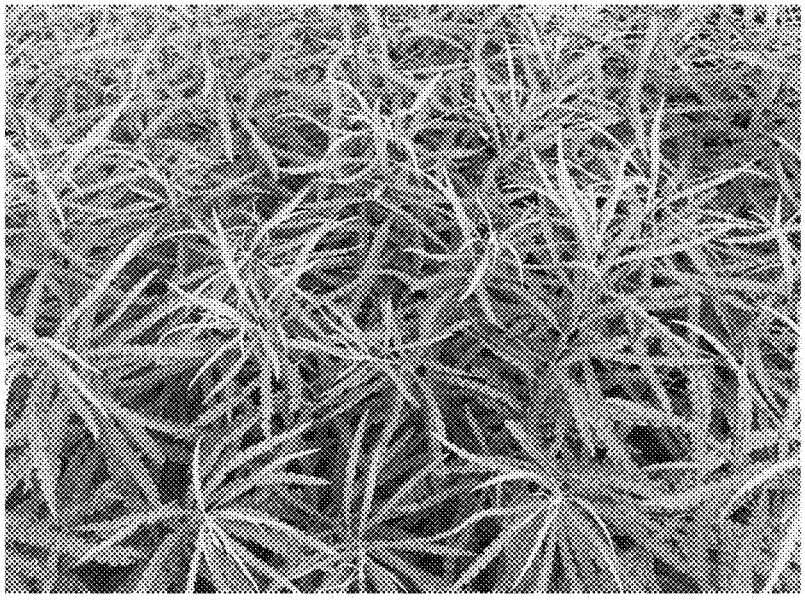
FIG. 1 shows a close-up view of the blue-tinted foliage of mature *Comptonia peregrina* 'Blue Sea'.
Figure 2:
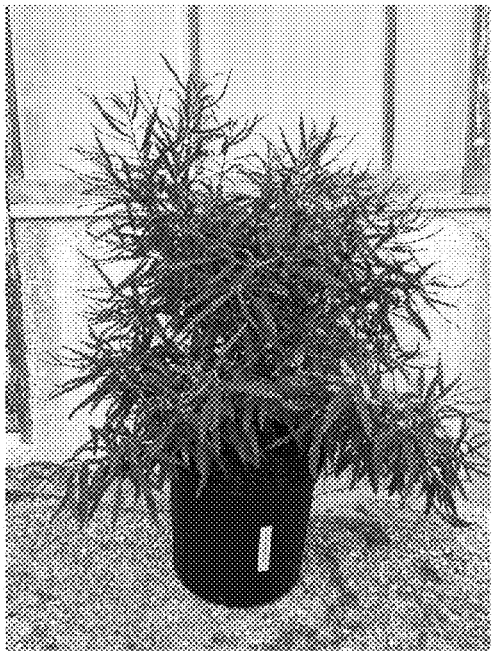
FIG. 2 shows a side-perspective view of a mature plant of *Comptonia peregrina* 'Blue Sea' grown outside in a two-gallon container.
Figure 3:
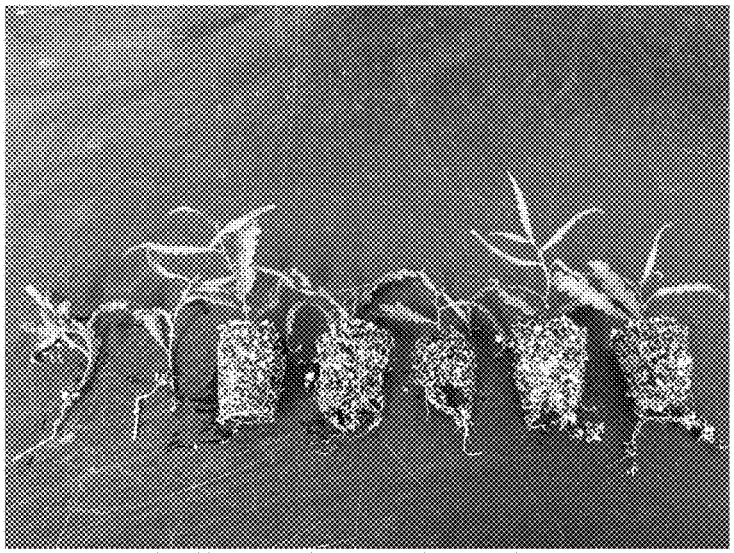
FIG. 3 shows rooted cuttings of *Comptonia peregrina* 'Blue Sea'.
Figure 4:
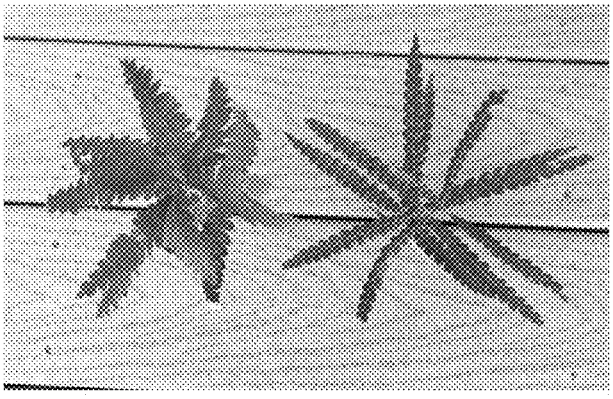
FIG. 4 shows a comparison between the foliage of wild *Comptonia peregrina* (left) and the narrow-leaved foliage *Comptonia peregrina* 'Blue Sea' (right).

The aforementioned photographs and following observations, measurements and values describe plants grown during summer in pots in an outdoor cold frame in Storrs, Conn. Plants used for the photographs and description were 3 years old. In the following detailed description, color references are made to The Royal Horticultural Society Colour Chart, 1995 Edition, except where general terms of ordinary dictionary significance are used.

Botanical classification: *Comptonia peregrina* cultivar 'Blue Sea'.

Parentage:

*Female, or seed, parent*.—Unnamed selection from Willington, Conn.

*Male, or pollen, parent*.—Unknown.

Propagation:

*Type*.—Softwood cutting, taken when shoot recently emerged from dormancy or from recently divided rhizomes and elongated to a length of 5 to 7.6 cm. 3000 (Hormodin 2) or 8000 ppm (Hormodin 3) IBA in talc.

*Time to initiate roots, summer*.—About 5 weeks at temperatures of about 75° F.

*Time to produce a rooted young plant, summer*.—About 8 weeks at temperatures of about 75° F.

*Root description*.—Fine.

*Rooting habit*.—Fibrous.

Plant description:

*Plant form and growth habit*.—Mounded and dense plant.

*Plant height*.—About 60-92 cm.

*Plant diameter* (*area of spread*).—About 60-92 cm.

*Vigor*.—Moderate.

Lateral branch description:

*Number*.—About 10-12 branches for a plant with a height of about 46 cm and diameter of about 60 cm.

*Length*.—About 10-20 cm.

*Diameter*.—About 2 mm.

*Internode length*.—About 5-10 mm.

*Color*.—Close to brown group 200D.

Leaf description:

*Arrangement*.—Alternate simple.

*Length*.—About 5-10 cm.

*Width*.—About 1-1.5 cm.

*Shape*.—Linear.

*Apex shape*.—Acute.

*Base shape*.—Acute.

*Margin type*.—Coarsely toothed.

*Texture, upper and lower surfaces*.—Minutely pubescent.

*Venation pattern*.—Pinnate.

*Fragrance*.—Sweet, most noticeably on warm sunny days.

*Color*.—Spring leaves, upper surface: Close to green 140B under high light conditions. Spring leaves, lower surface: Close to green 140B under high light conditions. Summer leaves, upper surface: Close to green 135A to 136A under high light conditions. Summer leaves, lower surface: Close to yellow green 148B under high light conditions. Fall leaves, upper surface: Close to greyed-red 180A to 178A. Fall leaves, lower surface: Ranges from yellow 9D to yellow-orange 18B.

*Petiole*.—Length: About 5 mm. Diameter: About 1 mm. Texture, upper and lower surfaces: minutely pubescent.

*Persistence of foliage*.—Deciduous.

*Glossiness of the leaf*.—Non-glossy.

Stem:

*Shape*.—Round.

*Surface texture*.—Pubescent.

*Color*.—Brown group 200D.

Flower description:

*Monoecious or dioecious*.—Monoecious.

*Flower arrangement and habit*.—Male catkins clustered at shoot tip in a few to several. Female flowers in small groups directly below male flowers.

*Fragrance*.—None.

*Natural flowering season*.—Early spring.

*Flower longevity*.—2 weeks.

*Inflorescence length*.—Male: About 2 cm. Female: About 7 mm.

*Inflorescence diameter*.—Male: About 6 mm. Female: About 8 mm.

*Inflorescence type*.—Male: Catkin. Female: Small apetalous with prominent stigmas.

*Number of flowers per inflorescence*.—Male: 60. Female: 40.

*Number of inflorescences per stem*.—Male: 8-10. Female: 0-2.

*Flower diameter*.—Male: About 3 mm. Female: About 1 mm.

*Flower length* (*height*).—Male: About 1-2 mm. Female: About 4 to 5 mm.

*Sepals* (*bract*).—Arrangement: Single subtending flower. Length: About 3 mm. Width: About 1 mm. Shape: Spade. Apex: Acuminate. Base: Broad. Margin: Minutely hairy. Texture, upper and lower surfaces: Pubescent. Color: Close to yellow green 149A transitions to orange 174C at the tip.

*Peduncles*.—Sessile.

*Pedicels*.—Sessile.

*Reproductive organs*.—Stamens: Quantity: 3 to 6. Anther shape: Oval. Anther length: About 0.5 mm. Anther color: Close to yellow green 149A. Pollen amount: Scarce, moderate. Pollen color: Close to yellow 8B. Pistils: Quantity: 1 per flower. Pistil length: About 5 mm. Style length: About 4 mm. Style color: Close to red purple 58A. Stigma color: Close to red purple 58A. Ovary color: Close to red purple 58A.

Fruit description:

*Shape*.—Elliptical.

*Size*.—5 mm.

*Color*.—Summer emergent, close to yellow-green 144B. Fall, close to greyed-orange 176B.

*Number of seeds*.—1.

Seeds description:

*Length*.—About 2-3 mm.

*Width*.—About 1-2 mm.

*Thickness*.—About 1-2 mm.

*Shape*.—Elliptical.

*Color*.—Close to greyed-orange 177B.

Garden performance: Plants of the new Sweetfern have been observed to have excellent garden performance and tolerate high light, full exposure, dry, infertile soils and summer temperatures above 90° F. and low temperatures of −20° F.

Pathogen and pest resistance: Plants of the new Sweetfern have not been shown to be resistant to pests and other pathogens common to Sweetfern plants.

It is claimed:

1. A new and distinct Sweetfern plant named ‘Blue Sea’, substantially as illustrated and described herein.

* * * * *